United States Patent [19]
Leff et al.

[11] Patent Number: 4,822,940
[45] Date of Patent: Apr. 18, 1989

[54] PROCESS FOR CONVERTING LIGHT HYDROCARBONS AND/OR NATURAL GAS TO LIQUID HYDROCARBONS

[75] Inventors: Alan A. Leff, Solon; Joseph E. Metcalfe, Aurora; Louis J. Velenyi, Lyndhurst; Christos Paparizos, Willowick, all of Ohio

[73] Assignee: The Standard Oil Company, Cleveland, Ohio

[21] Appl. No.: 86,097

[22] Filed: Aug. 17, 1987

[51] Int. Cl.$^4$ ............................................. C07C 2/00
[52] U.S. Cl. ................................... 585/415; 585/400; 585/500; 585/505; 585/538; 585/416; 585/943
[58] Field of Search ............... 585/943, 500, 400, 505, 585/538, 416, 415

[56] References Cited

U.S. PATENT DOCUMENTS

| | | | |
|---|---|---|---|
| 3,039,697 | 6/1963 | Kasbohm et al. | 260/679 |
| 3,156,733 | 11/1964 | Happel et al. | 260/679 |
| 3,410,922 | 11/1968 | Sanchez | 585/943 |
| 4,176,045 | 11/1979 | Leftin et al. | 208/48 R |
| 4,463,210 | 7/1984 | Steinberg et al. | 585/943 |
| 4,479,869 | 10/1984 | Petterson et al. | 208/130 |
| 4,520,217 | 5/1985 | Minet et al. | 585/415 |
| 4,665,259 | 5/1987 | Brazdil et al. | 585/943 |
| 4,672,144 | 6/1987 | Green | 585/943 |
| 4,704,496 | 11/1987 | Paparizos et al. | 585/943 |

OTHER PUBLICATIONS

Stanley, H. M. et al., "The Production of Gaseous, Liquid, and Solid Hydrocarbons from Methane, Part I-The Thermal Decomposition of Methane", Transactions, Journal of the Society of Chemical Industry, Jan. 11, 1929, vol. 48, pp. 1–8.

Fischer, F. et al., "The Synthesis of Benzene Hydrocarbons from Methane at Normal Pressure and Without a Catalyst", Brennstoff-Chemie, vol 9, No. 19, pp. 309–324 (1928).

Smith, H. M. et al., "Production of Motor Fuels from Natural Gas-I, Preliminary Report on the Pyrolysis of Methane", Report of Investigation, Dept. Commerce, Chemical Economy and Engineering Review, Jul.-/Aug. 1985, vol. 17, No. 78 (No. 190), pp. 47–48.

*Primary Examiner*—Asok Pal
*Attorney, Agent, or Firm*—Raymond F. Keller; David J. Untener; Larry W. Evans

[57] ABSTRACT

The present invention provides for a process for converting a feedstock comprising ethylene and/or acetylene to a product comprising liquid hydrocarbons. The process comprises maintaining said feedstock at a temperature in the range of about 700° C. to about 1000° C. for about 100 to about 1000 milliseconds to provide for said conversion. In one embodiment, the feedstock further comprises hydrogen. In another embodiment the feedstock comprises the product made by the process comprising heating a gaseous mixture comprising (i) hydrogen and (ii) natural gas and/or at least one light hydrocarbon at a temperature of at least about 1250° C. for an effective period of time to provide said feedstock. In still another embodiment, the feedstock further comprises natural gas and/or at least one light hydrocarbon in addition to said ethylene and/or acetylene.

26 Claims, No Drawings

PROCESS FOR CONVERTING LIGHT HYDROCARBONS AND/OR NATURAL GAS TO LIQUID HYDROCARBONS

TECHNICAL FIELD

This invention relates to a process for converting light hydrocarbons and/or natural gas to liquid hydrocarbons. More particularly, this invention relates to a process for converting a feedstock comprising ethylene and/or acetylene to a product comprising liquid hydrocarbons.

BACKGROUND OF THE INVENTION

The term "light hydrocarbon" is used herein to mean a hydrocarbon of from 1 to about 3 carbon atoms. Included are methane, ethane, ethylene, acetylene, propane, propylene and the like as well as mixtures of two or more thereof. The term "liquid hydrocarbon" refers to hydrocarbons that are substantially in the liquid form at a temperature of about 25° C. and a pressure of one atmosphere.

Natural gas typically contains about 40–95% methane depending on the particular source. Other constituents include about 10% of ethane with the balance being made up of $CO_2$ and smaller amounts of propane, the butanes, the pentanes, nitrogen, etc. Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Processed natural gas is used principally as a source of heat in residential, commercial and industrial service.

Most procesed natural gas is distributed through extensive pipeline distribution networks. As natural gas reserves in close proximity to gas usage decrease, new sources that are more distant require additional transportation. Many of these distant sources are not, however, amenable to transport by pipeline. For example, sources that are located in areas requiring economically unfeasible pipeline networks or in areas requiring transport across large bodies of water are not amenable to transport by pipeline. This problem has been addressed in several ways.

One approach has been to build a production facility at the site of the natural gas deposit to manufacture one specific product. This approach is limited as the natural gas can be used only for one product, preempting other feasible uses.

Another approach has been to liquefy the natural gas using cryogenic techniques and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about −162° C., transporting the gas, and revaporizing it are complex and energy intensive.

Another approach is to convert lower hydrocarbons (e.g., methane, natural gas) to $C_2+$ hydrocarbons using an arc discharge or an arc plasma process. With arc discharge, the feedstock is fed into the reactor to intersect with an electric arc struck between a graphite cathode and a metal (copper) anode. The reaction temperature is about 1500° C. with residence times of a few milliseconds before the reaction temperature is drastically reduced by quenching with water. Arc plasma is similar to arc discharge except that an auxiliary gas (e.g., hydrogen) is used as a heat carrier. The first successful commercial installation for electric arc cracking of lower hydrocarbons to acetylene was built by I.G. Farbenindustrie in 1940 at Huels. Other commercial arc discharge processes that have been installed were those of the DuPont Company which used a high-speed rotating arc and a Romanian process which produces ethylene and acetylene. The Huels and Romanian processes are believed to be still operating. The DuPont process was shut down in 1969. The arc plasma process has also been developed to industrial scale. See, Kirk-Othmer, "Encyclopedia of Chemical Technology", Third Edition, Volume 1 at pp. 214–218. A disadvantage with arc discharge is that large amounts of carbon are formed. An advantage of the arc plasma process is that acetylene can be produced from heavy feedstocks without the excessive carbon formation of a straight arc discharge process.

Still another approach involves the use of pyrolysis to convert methane and/or natural gas to higher molecular weight hydrocarbons (e.g., substantially liquid hydrocarbons) that can be easily handled and transported. Low temperature pyrolysis (e.g., to 250° C. and 500° C.) of hydrocarbon feedstocks to higher molecular weight hydrocarbons is described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$-$O_3$ mixtures, S, Se, $SO_3$, $N_2O$, NO, $NO_3$, F, etc. The conversion of methane and/or natural gas to higher molecular weight hydrocarbons at higher temperatures (e.g., above about 1200° C.) using pyrolysis has been suggested. These high-temperature processes are, however, energy intensive and have thus far not been developed to the point where high yields are obtained even with the use of catalysts. Some catalysts that are useful in these processes (e.g., chlorine) are corrosive under such operating conditions.

A common technique for pyrolyzing methane and/or natural gas involves the use of tubular reactors. The methane or natural gas flows through a tube placed inside a radiant and/or convective chamber of a furnace. The heat supplied to the methane or natural gas is dependent upon the surface area of the tubes, and thus only relatively small diameter tubes are typically used. During such pyrolysis, carbon tends to build up on the inner walls of the tubes. Because of the small diameter of the tubes, any deposited carbon forms a relatively thick layer and thereby severely inhibits further heat transfer. Tubular reactors can be used for cracking hydrocarbons like ethane or propane due to the fact that hydrocarbons of this type do not produce significant levels of carbon. However, the amount of carbon produced during the pyrolysis of methane or natural gas is substantially greater and thus to date it has not been feasible to pyrolyze methane or natural gas in these reactors for more than a few minutes or a few hours at a time because of carbon build-up on the inner walls of the tubes.

Stanley, H. M., et al, in "The Production of Gaseous, Liquid, and Solid Hydrocarbons from Methane. Part I—The Thermal Decomposition of Methane", Transactions, Journal of the Society of Chemical Industry, Jan. 11, 1929, Vol. 48, pp. 1–8, disclose that in the pyrolysis of methane the use of relatively long heating periods tends to cause methane to decompose into its elements (i.e., carbon and hydrogen) almost exclusively, and that such decomposition produces an accumulation of carbon that is unfavorable to the production of good yields of higher hydrocarbons. They indicate that this tendency is greatly increased by the use of large heating surfaces and by the presence of active materials such as nickel and iron. The solution they suggest is to use short periods of heating, as low as 0.4 second (400 milliseconds), temperatures of 1000°–1200° C., and relatively inactive heating surfaces, such as silica. They indicate that under such circumstances methane decomposes to produce numerous products including acetylene, ethylene, ethane, higher olefins, benzene and higher aromatic hydrocarbons, and that the production of carbon and hydrogen may become almost negligible.

U.S. Pat. No. 3,093,697 discloses a process for making acetylene by heating a mixture of hydrogen and a hydrocarbon stock (e.g., methane) at a reaction temperature that is dependent upon the particular hydrocarbon employed for about 0.01 to 0.05 second (10 to 50 milliseconds). The reference indicates that a reaction temperature of 2700° F. (1482° C.) to 2800° F. (1538° C.) is preferred for methane and that lower temperatures are preferred for higher molecular weight hydrocarbons. The molar ratio of hydrogen to hydrocarbon stock is between about 1 to 8 moles of hydrogen for each carbon atom of the hydrocarbon molecule.

U.S. Pat. No. 3,156,733 discloses a process for the pyrolysis of methane to acetylene and hydrogen. The process involves heating a methane-containing stream in a pyrolytic reaction zone at a maximum temperature above 1500° C. and sequentially withdrawing a gaseous product from said reaction zone and quenching said product rapidly to a temperature of about 600° C. or less.

U.S. Pat. No. 4,176,045 discloses a process for the production of olefins by steam-cracking normally liquid hydrocarbons in a tubular reactor wherein the residence time in the tubes is from about 0.02 to about 0.2 second (about 20 to about 200 milliseconds) and the formation of coke deposits in the tubular reactor is minimized.

U.S. Pat. No. 4,479,869 discloses a process for preheating a hydrocarbon feed (e.g., ethane, propane or mixtures thereof) to a steam-cracking furnace in a tubular reactor wherein the hydrocarbon feed is heated within the temperature range of about 370° C. to about 700° C. by indirect heat exchange with super-heated steam. The reference indicates that such preheating reduces the propensity for coke deposition and permits the production of ethylene from a wide range of feeds.

U.S. Pat. No. 4,520,217 discloses a process for producing light aromatics from a feedstock comprising one or more of the natural gas liquid components which comprises: (1) pyrolyzing the feedstock in a first pyrolysis zone at a temperature of about 620° C. to a temperature in excess of about 750° C. for less than about one second (1000 milliseconds); (2) admixing the pyrolyzed feedstock with a pyrolyzed recycle stream comprising $C_{2-4}$ hydrocarbons such that the sensible heat of the admixture is sufficient to initiate the reaction of forming light aromatics; (3) quenching the reacting admixture; (4) separating the reacted admixture into a $C_8+$ tar and an offgas; (5) further separating the offgas into fractions comprising a light aromatic product and the recycle stream; and (6) pyrolyzing the recycle stream in a second pyrolysis zone to form the pyrolyzed recycle stream of step (2).

Chemical Economy and Engineering Review, July/August 1985, Vol. 17, No. 7.8 (No. 190), pp. 47–48, discloses that furnaces have been developed commercially for steam cracking a wide range of liquid hydrocarbon feedstocks using process reaction times in the range of 0.05 to 0.1 second (50–100 milliseconds). This publication indicates that the use of these furnaces permits substantial increases in the yield of olefins—ethylene, propylene, butadiene—while decreasing production of less-desirable co-products.

SUMMARY OF THE INVENTION

The present invention provides for a process for converting a feedstock comprising ethylene and/or acetylene to a product comprising liquid hydrocarbons. The process comprises maintaining said feedstock at a temperature in the range of about 700° C. to about 1000° C. for about 100 to about 1000 milliseconds to provide for said conversion. In one embodiment, the feedstock further comprises hydrogen. In another embodiment the feedstock comprises the product made by the process comprising heating a gaseous mixture comprising (i) hydrogen and (ii) natural gas and/or at least one light hydrocarbon at a temperature of at least about 1250° C. for an effective period of time to provide said feedstock. In still another embodiment, the feedstock further comprises natural gas and/or at least one light hydrocarbon in addition to said ethylene and/or acetylene.

DESCRIPTION OF THE PREFERRED EMBODIMENTS

The feedstock comprises ethylene and/or acetylene. Preferably, the feedstock contains up to about 90% by volume acetylene, more preferably from about 30% to about 80% by volume acetylene; and up to about 90% by volume ethylene, more preferably from about 30% to about 50% by volume ethylene.

The feedstock can further comprise hydrogen. Hydrogen is preferably present in the feedstock at a level of up to about 90% by volume, more preferably at a level in the range of about 10% to about 80% by volume.

In a particularly preferred embodiment, the feedstock comprises ethylene, acetylene and hydrogen. Useful feedstock compositions comprise from about 1% to about 90% by volume ethylene, more preferably from about 10% to about 40% by volume ethylene; from about 1% to about 90% by volume acetylene, more preferably from about 20% to about 70% by volume acetylene; and from about 1% to about 90% by volume hydrogen, more preferably from about 10% to about 80% by volume hydrogen.

In addition to ethylene and/or acetylene, and optionally hydrogen, the feedstock can further comprise one or more other light hydrocarbons and/or natural gas. The light hydrocarbons include, for example, methane, ethane, propane, propylene, and the like as well as mixtures of two or more of said hydrocarbons. Methane and/or natural gas are preferred. The natural gas can be either wellhead natural gas or processed natural gas, as discussed above.

The feedstock can be diluted with carbon dioxide and/or carbon monoxide. It can also be diluted with nitrogen and other inert gases (e.g., noble gases such as helium, neon, argon, etc.). The mole ratio of carbon dioxide, carbon monoxide and/or inert gases to light hydrocarbon in the feedstock can range up to about 10 moles each per mole of light hydrocarbon, but is preferably less than about 3 moles of each per mole of light hydrocarbon.

In one embodiment of the invention, the feedstock is prepared by a process comprising heating a gaseous mixture comprising (i) hydrogen and (ii) natural gas and/or at least one light hydrocarbon at a temperature of at least about 1250° C., preferably about 1300° C. to about 1700° C., for an effective period of time to provide said feedstock. This period of time is preferably from about 0.5 to about 100 milliseconds, more preferably from about 5 to about 20 milliseconds. The light hydrocarbons can be, for example, methane, ethane, propane, propylene, and the like as well as mixtures of two or more of said hydrocarbons. The natural gas can be either wellhead natural gas or processed natural gas, as discussed above. Methane and/or natural gas are preferred. The gaseous mixture can be diluted with carbon dioxide and carbon monoxide. It can also be diluted with nitrogen or other inert gases (e.g., noble gases such as helium, neon, argon, etc.). This gaseous mixture preferably contains at least about 50% by volume methane, more preferably from about 50% to about 90% by volum methane. Hydrogen can be present at a level of up to about 70% by volume, and is preferably present at a level in the range of about 5% to about 50% by volume.

The temperature at which the feedstock is maintained in accordance with the inventive process is preferably in the range of about 700° C. to about 1000° C., more preferably about 750° C. to about 980° C., more preferably about 800° C. to about 900° C. In one embodiment of the invention the temperature of the feedstock prior to commencing the inventive process is below the temperature employed in said process, thus the feedstock is heated until the desired temperature is achieved. In another embodiment of the invention the temperature of the feedstock prior to commencing the inventive process is above the temperature employed in the inventive process, thus the feedstock is quenched or cooled until the desired temperature is achieved.

The period of time for maintaining the feedstock at the desired operating temperature in accordance with the inventive process is generally a time which is sufficient to provide the desired conversion to higher molecular weight liquid hydrocarbon products. However, this reaction time or residence time should not be so long as to provide sufficient time for the products obtained to decompose. Accordingly, the reaction time or residence time is preferably in the range of from about 100 to about 1000 milliseconds, more preferably from about 100 to about 600 milliseconds, more preferably from about 100 to about 500 millisec onds, more preferably from about 200 to about 350 milliseconds.

The inventive process can be conducted at subatmospheric, atmospheric or at elevated pressures up to about 50 atmospheres. Generally, the process is conducted at a pressure of from about 1 to about 10 atmospheres, and more generally at about 1 or 2 atmospheres.

In one embodiment of the invention, a two-step process for converting a gaseous mixture comprising (i) hydrogen and (ii) at least one light hydrocarbon and/or natural gas to a product comprising liquid hydrocarbons is provided. This process comprises the steps of (A) heating the gaseous mixture at a temperature of at least about 1250° C., preferably about 1300° C. to about 1700° C., for an effective period of time, preferably about 0.05 to about 100 milliseconds, more preferably about 5 to about 20 milliseconds, to form a feedstock comprising (i) hydrogen and (ii) ethylene and/or acetylene; and (B) quenching said feedstock to a temperature in the range of about 700° C. t about 1000° C., preferably about 750° C. to about 980° C., for about 100 to about 1000 milliseconds, preferably about 100 to about 600 milliseconds, more preferably about 100 to about 500 milliseconds, more preferably from about 200 to about 350 milliseconds to form said product.

In another embodiment, a two-step process for converting a gaseous mixture comprising (i) hydrogen and (ii) at least one light hydrocarbon and/or natural gas to a product comprising liquid hydrocarbons is provided. This process comprises the steps of (A) heating the gaseous mixture at a temperature of at least about 1250° C., preferably about 1300° C. to about 1700° C., for an effective period of time, preferably about 0.05 to about 100 milliseconds, more preferably about 5 to about 20 milliseconds, to form a feedstock comprising (i) hydrogen and (ii) ethylene and/or acetylene; and (B) quenching a second gaseous mixture comprising (i) said feedstock and (ii) at least one light hydrocarbon and/or natural gas to a temperature of about 700° C. to about 1000° C., preferably about 750° C. to about 980° C., for about 100 to about 1000 milliseconds, preferably about 100 to about 600 milliseconds, more preferably about 100 to about 500 milliseconds, more preferably from about 200 to about 350 milliseconds to form said product.

The overall composition of the hydrocarbon products produced in accordance with the inventive process may vary somewhat depending upon the nature (composition) of the gaseous mixture or feedstock that is initially used, and the conditions under which it is processed. The hydrocarbon products generally consist of mixtures of both aliphatic and aromatic materials. Since the inventive process is well-suited to a continuous, cyclic process, the lighter weight gaseous hydrocarbon products such as ethane, propane, etc., can be separated from the more desirable higher molecular weight liquid hydrocarbon products and recycled in the process for further conversion to higher molecular weight liquid hydrocarbon products. Unsaturated hydrocarbons such as ethylene, acetylene, propene, etc., may be present in the gaseous hydrocarbon products obtained in this invention and these may be recycled through the process for conversion to higher molecular weight liquid products.

Preferred hydrocarbon products made by the inventive process are aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms.

The apparatus that can be used in the inventive process can be any conventional pyrolysis reactor system that is adapted to the specific gaseous reactants and hydrocarbon products provided for in the inventive process. Such pyrolysis reactors include fired tubular heaters, pebble-bed heaters and regenerative furnaces, but fired tubular heaters are the generally preferred type of reactor. These reactors can be made from a variety of materials which can withstand high temperatures. In embodiments of the invention wherein a two-step process is employed, it is preferred to use a tubular reactor with a relatively narrow first section and a relatively wider second section to provide for different reaction or residence times; these sections would also have independent temperature controls to provide for different operational temperatures in each section. A more detailed description of such apparatus can be found in the Encyclopedia of Chemical Technology, Kirk and Othmer, Ed. Third Edition, Vol. 9, pp. 400–11 which is incorporated herein by reference. The design and construction of such apparatus is within the skill of the art and thus need not be described further herein.

In order to further illustrate the present invention, the following examples are provided. Unless otherwise indicated in the following examples and elsewhere in the specification and claims, all parts and percentages of the products are by weight, and those of the feeds are by volume; all temperatures are in degrees centigrade.

In each of the following examples, gaseous feedstocks were pyrolyzed with the result being the formation of a mixture of liquid and gaseous products. The operating parameters, feedstocks and products are indicated in the tables below. The "liquids" identified in the tables were those materials which condensed in containers cooled with dry ice and acetone. The weight percentage of the liquid products was calculated by weighing the liquids formed and dividing that weight by the amount of hydrocarbon in the feed composition and multiplying by 100. The selectivity was defined by dividing the weight of product formed by the weight of hydrocarbon feed converted and multiplying by 100. The conversion was defined by dividing the hydrocarbon that was converted by the hydrocarbon in the feed and multiplying by 100. The gases that were obtained from the process were analyzed using a gas chromatograph.

In Examples 1–25, a gaseous feedstock was introduced into an alpha-silicon carbide tubular reactor (6 mm I.D.) that was surrounded by an electric furnace to provide the desired temperature. The gaseous feedstock was advanced through the tubular reactor and the exiting liquid product was collected in containers cooled with dry ice and acetone. The residence time of gaseous materials in the tubular reactor was 300 milliseconds. The results for Examples 1–25 are indicated in Table I.

TABLE I

| Example | 1 | 2 | 3 | 4 | 5 | 6 | 7 | 8 | 9 | 10 | 11 | 12 | 13 |
|---|---|---|---|---|---|---|---|---|---|---|---|---|---|
| Feedstock (Vol. %): | | | | | | | | | | | | | |
| Acetylene | 16.6 | 16.6 | 16.6 | 25 | 25 | 25 | 25 | 25 | 33.4 | 33.4 | 33.4 | 33.4 | — |
| Ethylene | 33.4 | 33.4 | 33.4 | 25 | 25 | 25 | 25 | 25 | 16.6 | 16.6 | 16.6 | 16.6 | 50 |
| Hydrogen | 50 | 50 | 50 | 50 | 50 | 50 | 50 | 50 | 50 | 50 | 50 | 50 | 50 |
| Nitrogen | — | — | — | — | — | — | — | — | — | — | — | — | — |
| $CO_2$ | — | — | — | — | — | — | — | — | — | — | — | — | — |
| Temperature, °C. | 800 | 825 | 850 | 775 | 800 | 825 | 850 | 875 | 775 | 800 | 825 | 850 | 950 |
| Ethylene Conv. (Wt. %) | 17.3 | 20.6 | 21.1 | 15.2 | 18.2 | 21.7 | 23.5 | 25.1 | 13.8 | 13.9 | 15.3 | 14.0 | 50.3 |
| Acetylene Conv. (Wt. %) | 47.2 | 58.9 | 68.3 | 37.7 | 51.3 | 62.5 | 71.5 | 77.6 | 39.2 | 53.1 | 63.8 | 72.7 | — |
| Selectivity to Methane (Wt. %) | 8.8 | 10.1 | 13.6 | 5.5 | 8.1 | 9.3 | 11.2 | 13.3 | 5.1 | 7.5 | 9.7 | 10.7 | 14.6 |
| Selectivity to Ethane (Wt. %) | 17.1 | 16.4 | 16.4 | 10.4 | 11.3 | 9.7 | 9.3 | 8.4 | 6.3 | 6.7 | 6.7 | 6.6 | 5.6 |
| Selectivity to Acetylene (Wt. %) | — | — | — | — | — | — | — | — | — | — | — | — | 5.0 |
| Selectivity to Ethylene (Wt. %) | — | — | — | — | — | — | — | — | — | — | — | — | — |
| Selectivity to Carbon (Wt. %) | 0.14 | 0.16 | 0.2 | 0.25 | 0.27 | 0.21 | 0.25 | 0.35 | 0.2 | 0.2 | 0.2 | 0.22 | 0.28 |
| Selectivity to Liquids (Wt. %) | 71.8 | 67.7 | 75.2 | 82.4 | 84.3 | 82.0 | 79.4 | 81.7 | 96.8 | 95.1 | 88.6 | 87.7 | 59.1 |
| Liquid Yield (Wt. %) | 19.2 | 22.2 | 27.1 | 21.4 | 29.0 | 33.9 | 37.0 | 41.2 | 29.4 | 37.5 | 41.5 | 45.7 | 29.8 |

| Example | 14 | 15 | 16 | 17 | 18 | 19 | 20 | 21 | 22 | 23 | 24 | 25 |
|---|---|---|---|---|---|---|---|---|---|---|---|---|
| Feedstock (Vol. %): | | | | | | | | | | | | |
| Acetylene | — | — | — | 57.6 | 57.6 | 28.8 | 28.8 | 28.8 | 28.8 | 28.8 | 50 | 50 |
| Ethylene | 50 | 80 | 80 | — | — | 28.8 | 28.8 | 28.8 | 28.8 | 28.8 | 50 | 50 |
| Hydrogen | 50 | 20 | 20 | — | — | — | — | — | — | — | — | — |
| Nitrogen | — | — | — | 42.4 | 42.4 | 42.4 | 42.4 | 42.4 | — | — | — | — |
| $CO_2$ | — | — | — | — | — | — | — | — | 42.4 | 42.4 | — | — |
| Temperature, °C. | 925 | 950 | 925 | 750 | 775 | 825 | 850 | 875 | 825 | 850 | 750 | 775 |
| Ethylene Conv. (Wt. %) | 45.0 | 56.4 | 47.9 | — | — | 26.6 | 30.8 | 38.4 | 27.2 | 31.6 | 22.0 | 37.4 |
| Acetylene Conv. (Wt. %) | — | — | — | 45.0 | 69.6 | 61.5 | 70.4 | 78.8 | 64.1 | 71.6 | 51.4 | 79.5 |
| Selectivity to Methane (Wt. %) | 12.3 | 12.9 | 9.6 | 0.6 | 1.3 | 3.7 | 4.8 | 5.9 | 4.8 | 6.0 | 2.3 | 5.8 |
| Selectivity to Ethane (Wt. %) | 4.0 | 2.6 | 3.4 | — | — | 1.5 | 1.3 | 1.5 | 1.4 | 2.4 | 1.6 | 2.0 |
| Selectivity to | 3.6 | 3.7 | 2.9 | — | — | — | — | — | — | — | — | — |

TABLE I-continued

| | | | | | | | | | | | | |
|---|---|---|---|---|---|---|---|---|---|---|---|---|
| Acetylene (Wt. %) Selectivity to Ethylene (Wt. %) | — | — | — | 2.2 | 3.4 | — | — | — | — | — | — | — |
| Selectivity to Carbon (Wt. %) | Trace | 0.59 | 0.28 | 0.19 | 0.95 | 0.32 | 0.43 | 1.1 | 0.45 | 0.65 | 0.17 | 0.28 |
| Selectivity to Liquids (Wt. %) | 59.4 | 66.8 | 65.6 | 100.3 | 87.8 | 89.2 | 88.3 | 84.1 | 90.0 | 89.6 | 93.9 | 86.6 |
| Liquid Yield (Wt. %) | 24.4 | 37.7 | 31.4 | 45.1 | 61.1 | 96.2 | 95.7 | 95.3 | 40.5 | 45.6 | 34.0 | 50.0 |

Examples 1-25 demonstrate that significant levels of liquid product can be obtained by pyrolyzing gaseous feedstocks containing ethylene and/or acetylene in accordance with the invention. These examples also demonstrate that such pyrolysis can be effected with relatively low levels of carbon formation.

Examples 26-27 are illustrative of a two-step process wherein a methane/hydrogen mixture is pyrolyzed in a high-temperature, low-residence-time first step to form an intermediate product, and then the intermediate product is combined with natural gas and pyrolyzed in a low-temperature longer-residence-time second step. Example 28 is provided for comparative purposes; in this example the second step was not conducted. In the first step, a tubular reactor (3 mm I.D. alpha-silicon carbide) that was surrounded by an electric furnace to provide the temperature indicated in the table was used. The methane/hydrogen mixture was advanced through this first reactor and the exiting product or effluent was collected in dry-ice, acetone-cooled containers. For Example 28, the effluent was analyzed as indicated in the table. For Examples 26-27, the effluent was combined with a natural gas stream. The natural gas stream had the following analysis: 77.2% by volume methane, 6.7% by volume ethane, 3.4% by volume propane, and 12.7% by volume carbon dioxide. The effluent/natural gas mixture was introduced into a second tubular reactor (13 mm I.D. quartz) That was also surrounded by an electric furnace to provide the temperature indicated in the table. The effluent/natural gas mixture was advanced through the second tubular reactor and the exiting liquid product was collected in dry-ice, acetone-cooled containers. The results are indicated in Table II.

TABLE II

| Example | 26 | 27 | 28 |
|---|---|---|---|
| Temperature °C. | | | |
| First Reactor | 1393 | 1393 | 1393 |
| Second Reactor | 977 | 977 | — |
| Feedstock (Vol. %) | | | |
| First Reactor: | | | |
| Methane | 50 | 50 | 50 |
| Hydrogen | 50 | 50 | 50 |
| Second Reactor: | | | |
| No. 1 Effluent | 90.5 | 90.5 | — |
| Natural Gas | 9.5 | 9.5 | — |
| Residence Time (msec.) | | | |
| First Reactor | 14 | 14 | 13 |
| Second Reactor | 201 | 209 | — |
| Methane Conv. (%) | 19.2 | 20.5 | 24.5 |
| Ethane Conv. (%) | 79.4 | 80.0 | — |
| Propane Conv. (%) | 100 | 100 | — |
| Total Hydrocarbon Conv. (%) | 23.1 | 23.7 | 24.5 |
| Carbon Yield (%) | 0.2 | 0.3 | 0.3 |
| Liquid Yield (%) | 4.5 | 2.7 | 1.7 |
| Selectivity to (%): | | | |
| Liquid | 19.4 | 11.2 | 7.0 |
| Carbon | 1.0 | 1.1 | 1.2 |
| Ethane | — | — | 0.8 |
| Ethylene | 38.5 | 37.6 | 10.9 |

TABLE II-continued

| Example | 26 | 27 | 28 |
|---|---|---|---|
| Acetylene | 32.3 | 31.8 | 61.7 |
| Propylene | — | — | 0 |
| Propane | — | — | 1.9 |
| Butylene | — | — | 1.4 |
| Hydrogen | 11.7 | 12.5 | 14.7 |
| $C_2^+$ Selectivity (%) | 90.2 | 80.6 | 83.7 |
| $C_2^+$ Yield (%) | 20.8 | 19.1 | 20.5 |

Examples 26-28 indicate that an increased yield in liquid was obtained when the low-temperatue, longer-residence-time, second-step was used. All of the propane and most of the ethane was converted when the second step was used. Also, the overall carbon yield was extremely low.

Example 29 is illustrative of a two-step process wherein a mixture of methane and hydrogen is pyrolyzed in a first reactor at a high temperature for a relatively short period of time and then the effluent from the first step is pyrolyzed in a second reactor at a low temperature for a longer period of time. Example 30 is provided for comparative purposes; in this example the second step of the process was not conducted. In the first step a tubular reactor (3 mm I.D. alpha-silicon carbide) that was surrounded by an electric furnace to provide the temperature indicated in the table was used. The methane/hydrogen mixture was advanced through this reactor and the exiting product or effluent was collected. For Example 30, the liquid effluent was collected in dry-ice, acetone-cooled containers and samples were obtained and analyzed. For Example 29, the effluent was introduced into a second tubular reactor (17 mm I.D. quartz) that was also surrounded by an electric furnace to provide the temperature indicated in the table. The effluent was advanced through the second reactor and the exiting liquid product was collected in dry-ice, acetone-cooled containers. The results for Examples 29 and 30 are indicated in Table III.

TABLE III

| Example | 29 | 30 |
|---|---|---|
| Temperature °C. | | |
| First Reactor | 1440 | 1440 |
| Second Reactor | 900 | — |
| Feedstock (Vol. %) | | |
| First Reactor: | | |
| Methane | 50 | 50 |
| Hydrogen | 50 | 50 |
| Second Reactor: | | |
| No. 1 Effluent | 100 | — |
| Residence Time (msec.) | | |
| First Reactor | 12 | 13 |
| Second Reactor | 317 | — |
| Methane Conv. (%) | 41.4 | 45.4 |
| Carbon Yield (%) | 0.8 | 1.0 |
| Liquid Yield (%) | 9.0 | 6.0 |
| Selectivity to (%): | | |
| Liquid | 21.8 | 13.1 |
| Carbon | 1.9 | 2.1 |

TABLE III-continued

| Example | 29 | 30 |
|---|---|---|
| Ethane | 1.5 | 0 |
| Ethylene | 20.1 | 6.5 |
| Acetylene | 36.2 | 63.5 |
| Propylene | 0 | 0 |
| Propane | 0 | 1.4 |
| Butylene | 0 | 0.9 |
| Hydrogen | 12.6 | 14.3 |
| $C_2+$ Selectivity (%) | 79.6 | 85.4 |
| $C_2+$ Yield (%) | 33.0 | 38.8 |

Examples 29 and 30 demonstrate that a process employing a two-step pyrolysis with a first step at a high temperature (i.e., 1440° C.) and a short residence time (i.e., 12 milliseconds) followed by a second step at a low temperature (i.e., 900° C.) and longer residence time (317 milliseconds) (Example 29) provides higher yields of liquid without significant change in the yield of carbon when compared to a comparable process employing only a single step at a high temperature and a short residence time (Example 30).

An advantage of the invention is that light hydrocarbons can be converted to higher molecular weight liquid hydrocarbons at relatively high yields and at significantly low levels of carbon deposition.

While the invention has been explained in relation to its preferred embodiments, it is to be understood that the various modifications thereof will become apparent to those skilled in the art upon reading this specification. Therefore, it is to be understood that the invention disclosed herein is intended to cover such modifications as fall within the scope of the appended claims.

We claim:

1. A process for converting a feedstock comprising (i) hydrogen and (ii) ethylene and/or acetylene to a product comprising liquid hydrocarbons, the process comprising maintaining said feedstock in the absence or a catalyst at a temperature in the range of about 700° C. to about 1000° C. for about 100 to about 1000 millisecond.

2. The process of claim 1 wherein said feedstock comprises the product made by the process comprising heating a gaseous mixture comprising (i) hydrogen and (ii) natural gas and/or at least one light hydrocarbon at a temperture of at least about 1250° C. for an effective period of time to provide said feedstock.

3. The process of claim 1 wherein said feedstock further comprises natural gas and/or at least one light hydrocarbon in addition to said ethylene and/or acetylene.

4. The process of claim 3 wherein said feedstock further comprises hydrogen.

5. The process of claim 1 wherein said temperature is in the range of about 750° C. to about 980° C.

6. The process of claim 1 wherein said feedstock is heated for about 100 to about 600 milliseconds.

7. The process of claim 1 wherein said feedstock is heated for about 100 to about 500 milliseconds.

8. The process of claim 1 wherein said feedstock is heated for about 200 to about 350 milliseconds.

9. The process of claim 1 wherein said feedstock comprises up to about 90% by volume acetylene.

10. The process of claim 1 wherein said feedstock comprises up to about 90% by volume ethylene.

11. The process of claim 1 wherein said feedstock comprises up to about 90% by volume hydrogen.

12. The process of claim 1 wherein said feedstock comprises from about 1% to about 90% by volume ethylene, from about 1% to about 90% by volume acetylene, and from about 1% to about 90% by volume hydrogen.

13. The process of claim 2 wherein said gaseous mixture is heated at a temperature in the range of about 1300° C. to about 1700° C.

14. The process of claim 2 wherein said gaseous mixture is heated for about 0.5 to about 100 milliseconds.

15. The process of claim 2 wherein said gaseous mixture is heated for about 5 to about 20 milliseconds.

16. The process of claim 2 wherein said gaseous mixture comprises up to about 70% by volume hydrogen.

17. The process of claim 2 wherein said gaseous mixture comprises from about 5% to about 50% by volume hydrogen.

18. The process of claim 2 wherein said gaseous mixture comprises methane.

19. The process of claim 2 wherein said gaseous mixture comprises natural gas.

20. The process of claim 3 wherein said light hydrocarbon comprises methane.

21. The process of claim 3 wherein said feedstock further comprises natural gas.

22. A process for converting a feedstock comprising hydrogen, ethylene and acetylene to a product comprising liquid hydrocarbons, the process comprising maintaining said feedstock in the absence of a catalyst at a temperature in the range of about 750° C. to about 980° C. for about 100 to about 600 milliseconds.

23. A process for converting a feedstock comprising hydrogen, ethylene and acetylene to a product comprising liquid hydrocarbons, the process comprising maintaining said feedstock in the absence of a catalyst at a temperature in the range of about 750° C. to about 980° C. for about 200 to about 350 milliseconds.

24. A process for converting a feedstock comprising hydrogen, ethylene and acetylene to a product comprising liquid hydrocarbons, the process comprising maintaining said feedstock in the absence of a catalyst at a temperature in the range of about 800° C. to about 900° C. for about 100 to about 600 milliseconds.

25. A process for converting a gaseous mixture comprising (i) hydrogen and (ii) at least one light hydrocarbon and/or natural gas to a product comprising liquid hydrocarbons, the process comprising:
  (A) heating said gaseous mixture at a temperature of at least about 1250° C. for an effective period of time to form a feedstock comprising (i) hydrogen and (ii) ethylene and/or acetylene; and
  (B) quenching said feedstock in the absence of a catalyst to a temperature in the range of about 700° C. to about 1000° C. for about 100 to about 1000 milliseconds to form said product.

26. A process for converting a gaseous mixture comprising (i) hydrogen and (ii) at least one light hydrocarbon and/or natural gas to a product comprising liquid hydrocarbons, the process comprising:
  (A) heating said gaseous mixture at a temperature of at least about 1250° C. for an effective period of time to form a feedstock comprising (i) hydrogen and (ii) ethylene and/or acetylene; and
  (B) quenching a second gaseous mixture comprising (i) said feedstock and (ii) at least one light hydrocarbon and/or natural gas in the absence of a catalyst to a temperature of about 700° C. to about 1000° C. for about 100 to about 1000 milliseconds to form said product.

* * * * *